(12) United States Patent
Leutz et al.

(10) Patent No.: US 6,346,266 B2
(45) Date of Patent: *Feb. 12, 2002

(54) PLASTER WITH LONG-AFTERGLOW IMPRINT

(75) Inventors: Reiner Leutz, Reinbek; Witta Bruss; Jürgen Bosse, both of Hamburg, all of (DE)

(73) Assignee: Beiersdorf AG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/036,476

(22) Filed: Mar. 6, 1998

(30) Foreign Application Priority Data

Mar. 8, 1997 (DE) .......................................... 197 09 606

(51) Int. Cl.⁷ ............................ A61K 9/70; A61L 15/00; B32B 3/14; B32B 3/16; B32B 15/04
(52) U.S. Cl. ...................... 424/443; 424/445; 424/447; 424/448; 424/449; 428/78; 428/343
(58) Field of Search ................................. 424/443, 445, 424/447, 448, 449; 428/78, 343

(56) References Cited

U.S. PATENT DOCUMENTS

| 4,423,101 A | * | 12/1983 | Willstead ..................... 428/76 |
| 4,944,040 A | * | 7/1990 | Riedel et al. ..................... 2/15 |
| 5,275,870 A | * | 1/1994 | Halope et al. .............. 428/199 |
| 5,858,495 A | * | 1/1999 | Eikmeier et al. .......... 428/40.1 |

FOREIGN PATENT DOCUMENTS

| BE | 1 009 757 A | 8/1997 |
| DE | 545 722 | 2/1932 |
| DE | 296 14 078 U1 | 11/1996 |
| DE | 295 18 174 U1 | 1/1997 |
| GB | 2 217 206 A | 10/1989 |
| WO | 94/17766 | 8/1994 |

* cited by examiner

*Primary Examiner*—Shelly A. Dodson
(74) *Attorney, Agent, or Firm*—Norris McLaughlin & Marcus

(57) ABSTRACT

Plaster for adhesive bonding to the skin, in particular for the covering of relatively small wounds, consisting of a support material which is provided on its bottom side with a dermatologically compatible self-adhesive layer, characterized in that all or part of the top side of the support material bears a long-afterglow imprint consisting of a coating system into which a long-afterglow pigment has been incorporated.

12 Claims, No Drawings

PLASTER WITH LONG-AFTERGLOW IMPRINT

The invention relates to the further development of known plasters.

It is common practice to use plasters for covering wounds. The plasters consist of a support material which is provided on one side with a self-adhesive layer. In most cases, a wound covering is applied to this self-adhesive coating. In order to ensure that handling is straightforward, the self-adhesive coating is, furthermore, covered with a protective layer made of film, for example. Individual plasters are then punched out in various shapes from a roll and are sealed in paper. The punched shapes are geometrically regular forms such as rectangles or circles, for example.

German Utility Model DE U 74 20 413 describes a badge which on its visible surface has a two-dimensional or three-dimensional reproduction of at least one figured representation which is familiar to and preferably popular with children, which badge is characterized in that it is designed as a wound plaster having a cover layer, made of material which is gentle on wounds and/or promotes healing and/or breathes, which forms a support material for the figured representation and has regions that can stuck to the skin.

However, this type of representation always involves a conventional type of impression. No special optical effect can be achieved with it.

However, in general, plasters have predominantly no impression on the opposite side of the plaster support material from the body.

Only quite recently have comparable plasters been found on the market. Thus so-called Junior-Strips®, bearing an impression on a conventional form of plaster, are sold, this impression enjoying very great popularity especially among children. This impression usually consists of the representation of a cartoon character.

In spite of their undisputed advantages when used to cover relatively small wounds, known types of plaster are rather unpopular with adolescents and children, since there are negative associations such as pain, possibly bleeding and injury associated with the plaster.

In addition, conventional plasters have a dull appearance and are therefore unattractive to children.

In order to raise the visual stimulus for children and especially for adolescents, the company Kendall Futuro markets in the U.S., under the brand name Curad®, a plaster having a PVC film as support. The upper side of the support material carries over its full area an imprint which is most probably applied in random flexographic printing and which is intended to have afterglow (phosphorescent) properties. Tests with this plaster, however, have shown that the imprint is extremely short-lived and, moreover, has only a very weak afterglow.

In addition, the company Siebdruck Bischoff in Muggensturm produces long-afterglow safety guidance systems and safety signs. The support materials include 100 $\mu$m thick PVC films with a self-adhesive coating that are printed by sheet-fed screen printing with a coating system comprising a pigment having long-afterglow properties. The pigments employed in this system are based on alkaline earth metal aluminates that contain rare earth elements.

The object of the invention was, in particular for adolescents and children, to provide a plaster which is no longer unpopular with the said groups of individuals but which, instead, they find very interesting, and to do this with the simplest of means. In particular, the invention is directed towards the possibility of being able to use the plasters according to the invention to cover open wounds on the surface of the skin, in order to prevent unwanted consequences such as infection.

This object is achieved by a plaster as described in more detail in the claims.

The plasters comprise a support material, preferably a polyethylene film, which over all or part of its top side has a long-afterglow imprint comprising a coating system into which a long-afterglow pigment has been incorporated, and is provided on the bottom side with a dermatologically compatible self-adhesive layer.

Besides the said films, however, all materials suitable for the skin, for printing and for coating with a self-adhesive composition can be used as the support material. Other than films, supports of outstanding suitability include wovens, nonwovens or composites of these materials, with the proviso that the requirements placed on the support material—namely flexibility, printability and confirmity—are met.

In addition, the support material is advantageously white in coloration and/or has a white underlay or imprint.

In a preferred embodiment, the plaster is provided with a wound pad on the adhesive side of the support material, the wound pad being smaller than the bond surface and being applied in the centre of the support material.

In order to protect the wound pad against contamination and dirt, the support material side which is rendered self-adhesive may be provided with at least one tear-off cover sheet as a protective covering.

In a further preferred embodiment, the geometric shape of the support material substantially coincides with the outer contours of the imprint situated on the top side of the support material.

The coating system used is preferably a transparent, thermally drying coating system obtainable, for example, from the company SICPA Druckfarben GmbH, Backnang. Also suitable, however, are electron election beam crosslinking coating systems or UV coating systems.

The long-afterglow pigment is mixed into the coating system, especially with a proportion of 1:1. The pigment is incorporated into the coating system, with or without the use of a thickener, so as to ensure optimum homogeneity and immobility.

The afterglow intensity of the said mixture depends on the particle size distribution and on the amount applied to the support material. The amount applied is a function of the design of the screen that is used for printing.

The long-afterglow pigment incorporated into the coating system is preferably a zinc sulphide compound doped with copper ions, especially Lumilx® Effekt grun N-L (special-effect green N-L) from the company Riedel-de Häen. Pigments of this kind are able to absorb energy and to emit it again with a time delay, in the form of light quanta.

Also suitable, in general, are the long-afterglow pigments from the Lumilux® N group of the company Riedel-de Häen, which are polycrystalline, inorganic zinc sulphides or alkaline earth metal suphides. The latter in particular, which are able to bring about a red or blue afterglow effect, must be protected against direct contact with moisture through the use of an appropriate non-aqueous binder.

In order that the pigment may be employed, the long-afterglow pigment must meet the requirements for a medical product.

According to DIN 53160, no colorant and no optical brightener may pass from the respective medical product into the mouth, onto the mucous membranes or onto the skin. Therefore, the pigment must be fast to saliva and sweat.

DIN 71-3:1994 places a certain upper limit on the content of heavy metals. Since, however, it cannot be ruled out that the plaster of the invention will get into the mouths of small children, EN 648:1993, which represents a supplement to DIN 71-3, should also be observed, as is recommended in chapter XLVII of the BGVV Recommendation "Play products made from plastics and other polymers and from paper and cardboard" for toys which are intended to be, or which might foreseeably, taken into the mouth.

Finally, the pigments should also satisfy the European provisions regarding toy safety (EU Directive 88/378/EC).

In order to be sure of complying with the requirements set out above, the top side of the support material, which is where the long-afterglow imprint is located, should be provided with a mechanical barrier. The said barrier is preferably a plastic film or a varnish coat, such as a cationically curing UF flexgraphic print varnis. Alternatively, this protective layer can be produced by applying the printed image of the long-afterglow imprint in mirror image, by the counterprint process, and then attaching it to a laminate.

As a further preference, the coating system is blended with a thickener whose proportion, based on the coating system, can be between 1% by weight and 20% by weight, in particular between 2% by weight and 10% by weight. One possible thickener is, for example, Tixpaste UV (article No. 78-2-028) from the company SICPA Druckfarben GmbH, Backnang.

The thickener can be a mineral thickener, for example a colloida silica, or a thickener having a polymer structure, for example a silicone-based thickener, which has a property of crosslinking three-dimensionally.

The thickener which is present in the coating system prevents or retards sedimentation of the pigments, through an appropriate alteration in the viscosity in accordance with Stokes'law. The thickener therefore increases the afterglow effect of the coating system. Maximum afterglow intensity is found at between 2% by weight and 10% by weight thickener in the coating system.

When greater amounts of thickener are added to the coating system, i.e. proportions of 20% by weight or more, it is assumed that the thickener envelops the pigments so that the afterglow effect of the coating system is attenuated.

Also embraced by the invention, furthermore, is the process for producing a plaster. This process comprises the following steps:

a) at least one printing of the top side of the support material over its full area with white flexographic printing ink in order to increase the afterglow intensity of the pigments and at the same time to provide the finished product with opacity, b) if desired, printing of the part-areas of the top side of the support material that are not to be printed in the step d), by flexographic printing, c) preparing the mixture comprising a transparent coating system and the afterglow pigment, d) printing the top side of the support material with the mixture, preferably by screen printing, in the case of partial printing using a screen mechanism to fill in the white areas defined in step b), and e) if desired, aftercrosslinking the mixture by means of UV radiation, or thermally.

The printing which takes place in step a) of the process can be carried out by any customary variants. Possibly examples are flexographic, screen or intaglio printing. In addition to the screen printing set out in step d), however, the mixture can also be applied by patterned flexographic printing or intaglio printing.

In the case of partial application of the coating system, blended with the long-afterglow pigment, to the top side of the support material, virtually any desired original is conceivable. The selection of the motifs in this case can be guided by the age of the respective target group for the plaster of the invention. For young children, images of dolls, teddy-bears, stars, suns or the like may be conceived, and, for children, known characters from the wide world of cartoons, for example Asterix or Obelix, or else characters from the Donald Duck and Micky Mouse circle, or generally, themes corresponding to contemporary tastes, such as dinosaurs, and also, simply, representations of plants, animals or people.

The examples which have been listed are, however, only a small sample of the virtually unlimited range of possibilities. The skilled worker has a wide variety of possibilities for tailoring the design of the plaster according to the invention to the particular desired purpose or the particular intended target group. Further types of embodiment can be obtained by selecting a single-coloured or multicoloured support material, which allows controlled configuration of the plaster for an optimum appearance.

A further increase in the possibilities for variation can be achieved by printing those areas which are not provided with the long-afterglow imprint in any desired colours, either single-coloured or multicoloured, it being possible to tailor the selection of colours to the desired themes.

The external dimensions of the plaster according to the invention are within the range of those plasters conventionally used at present. In a preferred embodiment the horizontal axis of the plaster has a length of from 10 mm to 40 mm and the vertical axis has a length of from 40 mm to 80 mm.

In the eyes of the young, plasters according to the invention lose their actual character of being plasters. They are able to evoke the impression of a favourite sticker or even a kind of tattoo. Children and adolescents have very little aversion to this type of product, so that, further to the positive effect on the course of healing, the use of the plasters according to the invention at the same time provides a form of adornment.

With the aid of an example, the process of producing a plaster according to the invention will be presented below, without being intended to have any limiting effect whatsoever.

EXAMPLE

In order to produce the plasters, the support material, a 60 μm thick, transparent polyethylene plaster film, was first of all coated with a dermatologically compatible adhesive coat based on crosslinked polyacrylic acid derivatives, was provided with a wound pad and was lined with silicone treated paper which covers the adhesive coat. An adhesive composition of this type is disclosed in the document DE 27 43 979 C3. The top side of the support material was printed twice over its entire area, in the flexographic processs, with white flexographic printing ink (67S 826309 from the company Hostmann-Steinberg GmbH).

Subsequently, those regions of the support material surface which were not to be provided with long-afterglow motifs were printed, likewise in the flexographic printing process, with blue flexographic printing ink (63S 830809 from the company Hostmann-Steinberg GmbH).

In parallel to this a mixture was prepared from the pigment powder "UV Transparent Nachleuchtfarbe" (UV transparent afterglow colour) (article No. 78-2-133) and the coating material "UV Transparent Nachleuchtfarbe" (article No. 78-2-133-1), both from the company SICPA Druckfarben GmbH, Backnang. This transparent coating system was then mixed with the long-afterglow pigment Lumilux® Effekt grun N-L from Riedel-de Haen, in a ration of 1:1.

This system was additionally admixed with the thickener "Tixpaste UV" (article No. 78-2-028) from the company SICPA Druckfarben GmbH, Backnang, in a proportion of 5% by weight based on the system.

The previously defined areas were then provided with the mixture, using a special screen (having a mesh size of 77 mesh with a 40% open fraction), enabling controlled application to be made to the sites at which the afterglow is desired, with a very high applied amound of the mixture.

The plasters were then punched out using a rotary punch, sealed in paper in order to protect the plaster against external soiling or contamination, and finally wound up into a roll.

What is claimed is:

1. A plaster for adhesive bonding to the skin, comprising a support material which is provided on its bottom side with a dermatologically compatible self-adhesive layer and a wound pad, and wherein all or part of the top side of the support material bears a long-afterglow imprint comprising a coating system into which a long-afterglow pigment is incorporated.

2. Plaster according to claim 1, wherein the support material comprises a polyethylene film.

3. Plaster according to claim 1, wherein the support material is white in coloration or has a white underlay or imprint, or any combination thereof.

4. Plaster according to claim 1, wherein a wound pad which is smaller than the bond surface is applied to the adhesive side of the support material.

5. Plaster according to claim 1, wherein the wound pad is applied in the center of the support material.

6. Plaster according to claim 1, wherein the support material side which is rendered self-adhesive is provided with at least one tear-off cover sheet as a protective covering.

7. Plaster according to claim 1, wherein said pigment is a long-afterglow polycrystalline, inorganic zinc sulphide or alkaline metal sulphide.

8. Plaster according to claim 1, wherein said pigment is a zinc sulphide compound doped with copper ions.

9. Plaster according to claim 1, wherein a thickener has been added to the coating system.

10. Plaster according to claim 1, wherein the top side of the support material, including the long-afterglow imprint, is coated with a plastic film or a varnish coat.

11. Plaster according to claim 1, wherein the geometric shape of the support material substantially coincides with the outer contours of the imprint situated on the top side of the support material.

12. A process for producing a plaster comprised of a support material having a dermatologically compatible self-adhesive material and a wound pad on one side and a coating comprising a long-afterglow pigment on all or part of the other side, which comprises printing one side of said support material with a white flexographic printing ink by flexographic printing or screen printing and then printing all or part of the same side of said support material with a mixture comprising a transparent coating system into which a long-afterglow pigment has been incorporated, optionally crosslinking said coating system; coating the other side of said support material with said dermatologically compatible self-adhesive material and attaching a wound pad to the same side that is coated with the self-adhesive material.

* * * * *